US005866073A

United States Patent [19]
Sausa et al.

[11] Patent Number: 5,866,073
[45] Date of Patent: Feb. 2, 1999

[54] DETECTOR OF HALOGENATED COMPOUNDS BASED ON LASER PHOTOFRAGMENTATION/FRAGMENT STIMULATED EMISSION

[75] Inventors: Rosario C. Sausa, Bel Air, Md.; Josef B. Simeonsson, Iowa City, Iowa

[73] Assignee: The United States of America as represented by the Secretary of The Army, Washington, D.C.

[21] Appl. No.: 808,731

[22] Filed: Feb. 28, 1997

[51] Int. Cl.$^6$ ............................ G01N 21/01; G01N 21/63
[52] U.S. Cl. .................................. 422/82.05; 422/82.09; 422/82.11; 250/334; 250/338.5; 436/124; 436/125; 436/126; 436/172
[58] Field of Search .................................. 436/124–126, 436/171, 172, 183; 422/82.05, 82.09, 82.11, 83; 250/334, 338.5, 343

[56] References Cited

U.S. PATENT DOCUMENTS

| | | | |
|---|---|---|---|
| 4,555,627 | 11/1985 | McRae, Jr. | 250/334 |
| 4,909,990 | 3/1990 | Block et al. | 422/82.11 |
| 5,364,795 | 11/1994 | Sausa et al. | 436/106 |
| 5,373,160 | 12/1994 | Taylor | 250/338.5 |
| 5,443,793 | 8/1995 | Ehrlich et al. | 422/83 |

OTHER PUBLICATIONS

K. G. Anlauf et al., *Phys. Lett. A* 1967, 24, 208–210.
R. M. Benmair et al. *Chem. Phys. Lett.* 1983, 95, 72–77.
J. I. Selco et al. *J. Chem. Phys.* 1983, 79, 4083–4085.
F. P. Milanovich et al. *Anal. Instrum.* 1986, 15, 347–358.
M. Alden et al. *Opt. Lett.* 1989, 14, 305–307.
A. D. Sappey et al. *Appl. Phys. Lett.* 1989, 55, 1182–1184.
R. Buschner et al. *Proc. SPIE–Int. Soc. Opt. Eng.* 1992, 1714, 39–45.
R. Lange et al. *Proc. SPIE–Int. Soc. Opt. Eng.* 1992, 1714, 46–53.
J. B. Jeffries et al. *Appl. Phys. B* 1992, 55, 76–83.
G. A. Theriault et al. *Proc. SPIE–Int. Soc. Opt. Eng.* 1995, 2504, 75–83.
J. P. Kumer et al. *Proc. SPIE–Int. Soc. Opt. Eng.* 1995, 2366, 367–375.
Simeonsson et al., "Trace detection of ambient brominated compounds by laser–induced photofragmentation/fragment detection spectrometry", *Spectrochimica Acta*, vol. 49B, Nos. 12–14, pp. 1545–1555, Elsevier Science, Ltd., Great Britain, 1994.
Simeonsson et al., "Laser–Induced Photofragmentation/ Photoionization Spectrometry: A Method for Detecting Ambient Oxides of Nitrogen", *Analytical Chemistry*, vol. 66, No. 14, pp. 2272–2278, American Chemical Society, 1994.

(List continued on next page.)

*Primary Examiner*—Arlen Soderquist
*Attorney, Agent, or Firm*—Paul S. Clohan; U. John Biffoni

[57] ABSTRACT

A method and apparatus is provided for real-time detection of trace amounts of atmospheric and tropospheric halogen-containing compounds. The present invention can be used either for in situ detection or remote sensing. A laser is employed to induce photofragmentation of the halogenated molecules and facilitate detection of the characteristic atom fragment by stimulated emission spectrometry. For brominated compounds, the output of a single laser is tuned to the strong two-photon $4p^45p\ ^4D°_{3/2} \leftarrow 4p^{52}\ P°_{3/2}$ transition of Br at 260.634 nm. The Br atoms are subsequently detected by stimulated emission (SE) via the $4p^45p\ ^4D°_{3/2} \rightarrow 4p^45s\ ^4P_{5/2}$ transition at 844 nm. For comparison, the laser-induced fluorescence (LIF) signal at the same wavelength is also monitored. The SE signal is distinct from the fluorescence in that it is coherent, bidirectional, and propagates coaxially with the laser beam. As a result of photophysical amplification, it is approximately two orders of magnitude greater than the LIF signal. The present invention has been demonstrated for trace detection of $CHBr_3$ and $CHClBr_2$ in $N_2$ or air at total gas pressures of 1–760 Torr. Detection limits are in the parts-per-million range. The absorption cross section of the two-photon $4p^45p\ ^4D°_{3/2} \leftarrow 4p^{52}\ P°_{3/2}$ transition is estimated to be $3.8 \times 10^{-43}\ cm^4$.

13 Claims, 5 Drawing Sheets

OTHER PUBLICATIONS

Simeonsson et al., "Trace Detection of Nitrocompounds by ArF Laser Photofragmentation/Ionization Spectrometry", *Applied Spectroscopy*, vol. 47, No. 11, pp. 1907–1912, Society for Applied Spectroscopy, 1993.

Arepalli et al., "Detection of Cl Atoms and HCl Molecules by Resonantly Enhanced Multiphoton Ionization", *Chemical Physics Letters*, vol. 118, No. 1, pp. 88–92, Elsevier Science Publishers B.V., 1985.

Arepalli et al., "The Detection of Bromine Atoms by Resonant Multiphoton Ionization", *Chemical Physics Letters*, vol. 117, No. 1, pp. 64–66, Elsevier Science Publishers B.V., 1985.

McIlrath et al., "Two–photon lidar technique for remote sensing of atomic oxygen", *Applied Optics*, vol. 18, No. 3, pp. 316–319, Optical Society of America, 1979.

DETECTOR OF HALOGENATED COMPOUNDS BASED ON LASER PHOTOFRAGMENTATION/FRAGMENT STIMULATED EMISSION

STATEMENT OF GOVERNMENT INTEREST

The subject matter of the present application was developed by employees of the U.S. Government, Department of the Army, Army Research Laboratory, in the course of their employment. The invention described herein may be manufactured, used and licensed by or for the United States Government.

FIELD OF THE INVENTION

The present invention relates to a method and apparatus for real-time detection of trace amounts of atmospheric and tropospheric halogen-containing compounds, and more particularly relates to a method and apparatus for real-time detection of trace amounts of atmospheric and tropospheric halogenated compounds based on laser photofragmentation/fragment stimulated emission.

BACKGROUND OF THE INVENTION

In situ or remote detection and monitoring of trace amounts of halogen-containing compounds in real-time is critical to the safety of humans, wildlife, and the environment. Volatile halogenated organic compounds, particularly those containing chlorine (Cl) or bromine (Br), are of considerable environmental importance due to their stratospheric ozone depletion properties, their contributions to the global greenhouse effect and their utility as indicators of biological inputs in biogeochemical studies of marine and atmospheric systems. There are also developing concerns that chlorinated organics cause cancers in adults and adverse health and reproductive effects in the offspring of both humans and wildlife. As a result, the development of monitoring methods for halogenated species has received increasing attention.

The most common method used to determine halogenated species under ambient conditions is cryogenic preconcentration of the sample followed by gas chromatography with electron capture detection (GC-ECD). The method is very sensitive, part-per-trillion (ppt) in level, with absolute limits of detection of the halogen atom on the order of 1–100 pg, depending on the compound. Despite high sensitivity, the GC-ECD technique requires extensive sample manipulation and a long measurement cycle, typically about one hour. Other methods of detection include mass and ion mobility spectrometry. Although these methods are also sensitive, they are not conducive to real-time, in situ measurements since the sample needs to be retrieved into an analysis chamber. In addition, acquisition and analysis is relatively slow and the prior-art apparatus is not readily portable due to its size.

Laser-based methods offer the advantages of high sensitivity and speed for the real-time monitoring of small species such as atoms, diatomics, and triatomics. These methods include laser-induced multiphoton ionization and laser-induced fluorescence. These methods currently enjoy limited applications. Many halogen containing compounds are large and lack distinguishing spectral features or absences of any features in the ultraviolet-to-visible (UV-Vis) spectral region. In addition, dissociation processes of the target molecules subsequent to laser excitation competes with ionization or fluorescence processes, causing a decrease or absence of ionization or fluorescence detection signal. As a result of these limitations, other approaches have been sought to overcome these obstacles.

One successful approach involves the use of the laser photofragmentation/fragment detection spectrometry. Selected references include: (1) U.S. Pat. No. 5,364,795, issued to Sausa et al. on Nov. 15, 1994; (2) Simeonsson, Lemire, and Sausa, "Trace Detection of Nitrocompounds by ArF Laser Photofragmentation/Ionization Spectrometry," Applied Spectroscopy, Vol. 47, No. 11, p. 1907, 1993; (3) Simeonsson, Lemire, and Sausa, "Laser-Induced Photofragmentation/Photoionization Spectrometry: A Sensitive Method for Detecting Ambient Oxides of Nitrogen," Analytical Chemistry, Vol. 66, No. 14, p. 2272, 1994; (4) Simeonsson and Sausa, "Trace Detection of Ambient Brominated Compounds by Laser-Induced Photofragmentation Detection Spectrometry," Spectrochimica Acta, Vol. 49B, p. 1545, 1994; (5) Arepalli, Presser, Robie, and Gordon, "Detection of Cl Atoms and HCl molecules by Resonance-Enhanced Multiphoton Ionization," Chem. Phys. Lett., Vol. 118, p. 88, 1985; and (6) Arepalli, Presser, Robie, and Gordon, "Detection of Br atoms by REMPI," Chem. Phys. Lett., Vol. 117, p. 64, 1985; all of which are incorporated herein by reference.

In the laser photofragmentation/fragment detection approach, the target molecule is photolyzed to produce characteristic fragments, such as atoms and small molecules which can be detected by multiphoton ionization (PF/MPI) or laser-induced fluorescence (PF/LIF) since they possess favorable combination of usually strong optical transitions and sharp, well-resolved spectral features. However, PF/MPI is susceptible to high background noise as well as a high degree of interference due to nonresonant multiphoton ionization. For LIF, laser scatter can present a significant problem. Moreover, the collection of total LIF from the photofragment is difficult since it is isotropic and incoherent.

SUMMARY AND OBJECTS OF THE INVENTION

A one-laser photofragmentation/fragment detection approach is used when the analyte molecule does not lend itself to direct spectroscopic detection. This is often the case for large molecules which possess weak transitions or broad and poorly defined spectral features. Laser photolysis of large molecules results in the generation of characteristic fragments such as atoms and small molecules, e.g., diatomic and even triatomic species. These species possess favorable combination of usually strong optical transitions and sharp, well-resolved spectral features and can be generally detected by various techniques such as absorption, fluorescence, photoionization, or, as in the present invention, by stimulated emission. The photofragments are characteristic of the chemical composition of the precursor molecule and contribute to the selectivity of the analytical method. The photofragmentation process has a characteristic spectral dependence which may be exploited to further increase the selectivity of laser photofragmentation/fragment stimulation emission approach.

The present invention relates to a real-time monitoring of trace halogen containing compounds found in the atmosphere and the troposphere by detecting specific halogen containing fragments by a laser photofragmentation/fragment stimulated emission (PF/SE) technique. The device may be employed for either point detection or remote sensing.

PF/SE circumvents some of the problems encountered with PF/MPI or PF/LIF. Stimulated emission occurs subsequent to laser excitation in chemical systems in which the major processes of de-excitation are closed. The signal is photophysically amplified to produce signal intensity orders of magnitude greater than achievable with corresponding LIF. The SE signal is optically coherent and coaxial with the probe laser radiation. Furthermore, as the SE signal is bidirectional, it only requires "one window" access to the sample environment for point detection. It also has potential for remote applications since the detector can be placed at an extended distance from the probed region.

The present invention is a portable and rugged system which is highly specific to halogen-containing compounds, and can be manufactured into a sturdy and fieldable device. Laboratory demonstration has been achieved for $CHBr_3$ and $CHClBr_2$.

The object of this invention is to provide a laser-based sensitive detection method and apparatus employing one laser to photofragment the target molecule and also facilitate the detection of the characteristic fragment by stimulated emission.

It is a further object of the present invention to provide a laser photofragmentation/fragment detection by stimulated emission method for real-time sensing of atmospheric/tropospheric halogenated compounds in situ.

Still a further object of the present invention is to provide a laser photofragmentation/fragment detection by stimulated emission apparatus for in real-time, remote sensing of atmospheric/tropospheric halogenated compounds.

Other objects of the present invention will be apparent from the following detailed description of the invention.

DETAILED DESCRIPTION OF THE INVENTION

The best mode for the present invention encompasses a laser-based sensitive detection method and apparatus to photofragment the target molecule and also facilitate the detection of the characteristic fragment by stimulated emission.

Separate embodiments are disclosed: A point detection embodiment and a remote detection embodiment. For point detection, a hand-held probe, laser and data acquisition and analysis components are used. A fiber optic is coupled to the laser at one end and the hand-held probe at the other end. The probe consists of a casing with lens and concave mirror assembly. The fiber optic transmits the required radiation for both photolysis of the sample and for inducing the stimulated emission. As the stimulated emission is coherent and propagates coaxially with the laser beam in a bidirectional manner, a concave mirror is used to reflect and focus the forward signal back into the fiber optic. This signal, together with that propagated opposite the laser beam, is then transmitted back to the laser source. Beam separating mirrors and prisms are used to isolate the signal from the laser radiation. Detection is accomplished with a photomultiplier equipped with a narrow band interference filter or optical multichannel analyzer. The signal is displayed in real-time on a digital oscilloscope interfaced to a laptop computer.

For remote applications, the laser system is placed in a vehicle or plane. The laser may then be focussed to the region of interest from the source using a concave mirror with 20 meter or larger radius of curvature. In this case, the laser radiation is transmitted through the atmosphere or troposphere without use of fiber optic and the stimulated emission coaxial and opposite the laser radiation is collected at the source. Signal processing, acquisition, and analysis is performed similar to point detection.

The present invention has been shown to be useful. Moreover, the detection of $CF_3Br$ and $CF_3Br$ at a distance of two meters has been demonstrated with detection limits in the low parts-per-million range.

The specific features of the present invention are further set forth as follows.

BEST MODE: THE LASER PF/SE TECHNIQUE

Figure 1:
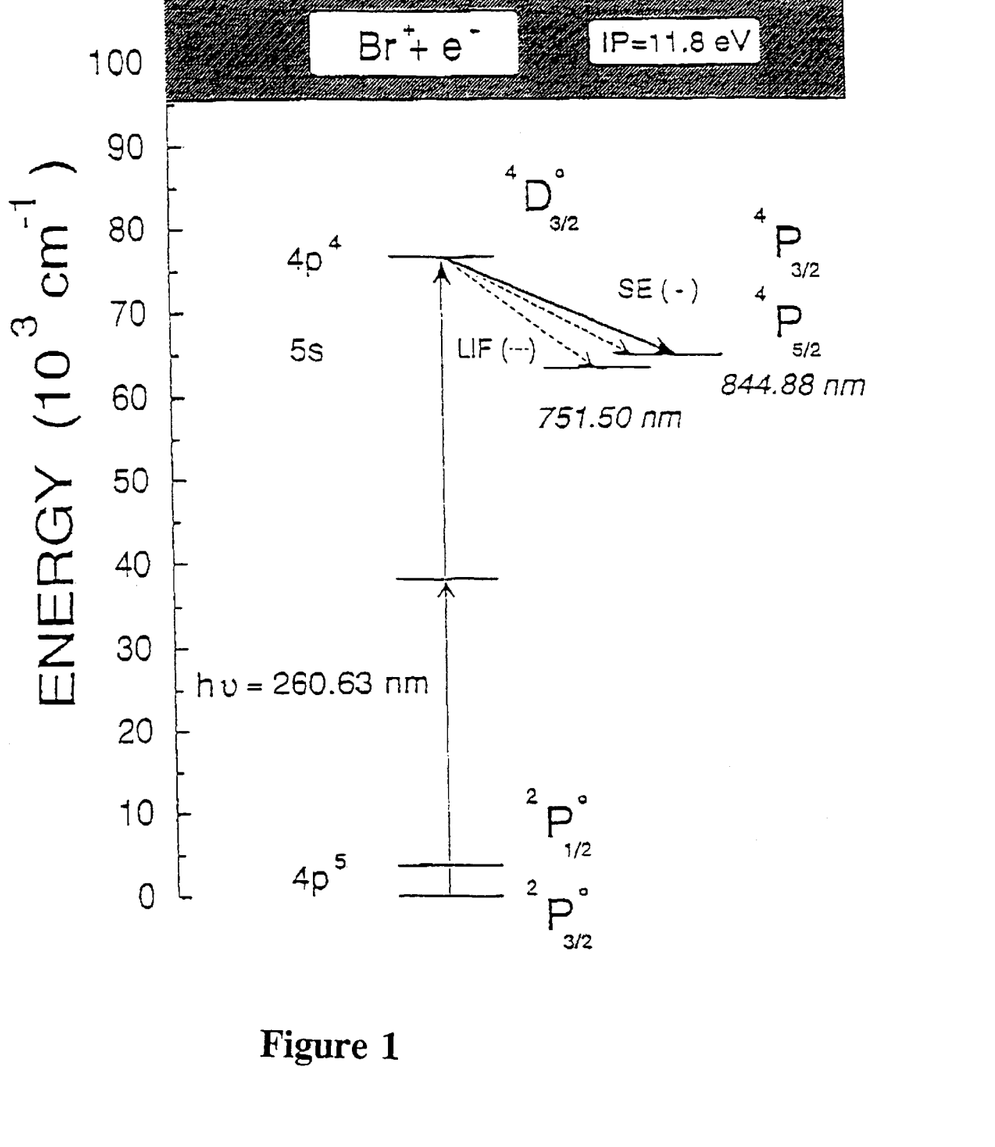
FIG. 1 is a partial energy level diagram showing pertinent states and two-photon transition of Br atom.

FIG. 1 is a partial potential energy level diagram for the Br atom. For the best operating mode, the precursor molecule is first photofragmented, yielding the Br atom in its ground ($^2P°_{3/2}$) and/or first excited ($^2P°_{1/2}$) state, and its corresponding companion radical (R), via the process $$R-Br \rightarrow R+Br(^2P°_{3/2,1/2}) \qquad (1)$$

This process requires modest laser energies, 100–500 µJ, since the atom is weakly bound to the main skeletal portion of the molecule. The Br atoms generated are then detected by SE involving the $4p^45p\ ^4D°_{3/2} \rightarrow 4p^45s\ (^4P_{5/2})$ transition near 844 nm. In this system, it is also possible to monitor fluorescence involving the $4p^45p\ ^4D°_{3/2} \rightarrow 4p^45s\ (^4P_{3/2}, ^4P_{5/2})$ transition at 751 and 844 nm, respectively.

The observed emission was verified to be SE: The emission appeared to meet an intensity threshold; was coherent in its propagation, as determined by its constant measured intensity close to, and away from, the cell; and was much stronger than the isotropically emitted LIF, being nearly two orders of magnitude greater when normalized for the observed solid angle. Further evidence that the observed emission was SE was the negligible emission observed at 751 nm as compared to 844 nm. While both transitions originate from the same $5p\ ^4D°_{3/2}$ state, only the 844 nm line showed significant SE emission. As the lower state of the transition at 751 nm is the lowest of the $^4P$ multiplet, establishing and maintaining a population inversion with this state is less probable due to collisional decay to the state from other states which spoils the gain. Stimulated emission to the $5s\ ^4P_{1/2}$ state of Br at 1014.3 nm was not verified due to the limited response of the PMT.

REMOTE SENSOR EMBODIMENT IMPLEMENTING THE PF/SE APPROACH

Figure 2:
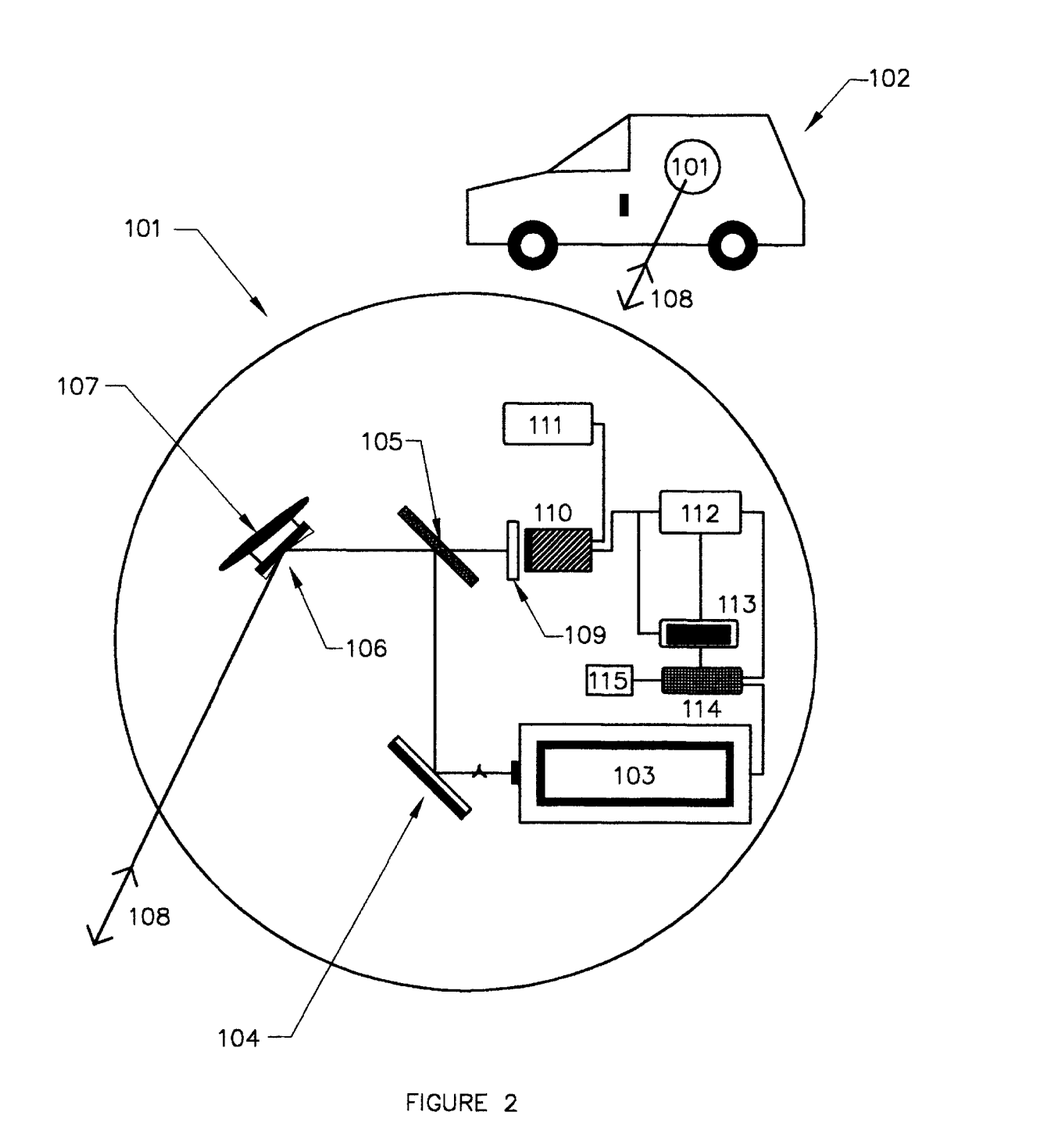
FIG. 2 is a block diagram illustrating the remote-sensing analyzer embodiment of present invention.

FIG. 2 is a block diagram of a remote-sensor embodiment 101. The sensor is housed inside a road vehicle or plane 102. A laser 103 provides the required radiation for the photofragmentation of the target species and also for inducing stimulated emission of the characteristic fragment. The radiation is steered with appropriate mirrors or prisms 104 onto a quartz substrate with antireflecting laser coating 105.

The coating allows reflection of the laser radiation and the transmission of all other radiation from the ultraviolet to near infrared. Other means, such as prisms, can also be used to separate the laser radiation from the induced stimulated emission signal. Mirror 105 reflects the laser radiation onto a curved mirror 106 with desired radius of curvature of about 10–20 meters, mounted on a x-y-z micropositioner 107. The positioner 107 allows for scanning the laser beam to the desired sensing location.

If the analyte or target molecule is present, photofragmentation with subsequent excitation results in amplified stimulated emission 108 as described above, and the emission, which is coaxial and opposite the laser radiation, is propagated back to the curved mirror 106, through the quartz substrate with antireflecting laser coating 105, through an interference filter 109, and onto a photodetector 110 powered by a variable voltage supply 111. Alternatively, a monochromator or optical multichannel analyzer may be substituted in place of the interference filter 109. The signal from the photodetector 110 is directed to a gated integrator 112 and possibly a digital oscilloscope 113 for real-time display. A laptop computer 114 interfaced to the gated integrator or boxcar 112 and possibly the oscilloscope 113 is used for system control, data acquisition, as well as analysis. Hard copies of the spectra are obtained by a printer or plotter 115 connected to the computer.

POINT DETECTION EMBODIMENT IMPLEMENTING THE PF/SE APPROACH

Figure 3:
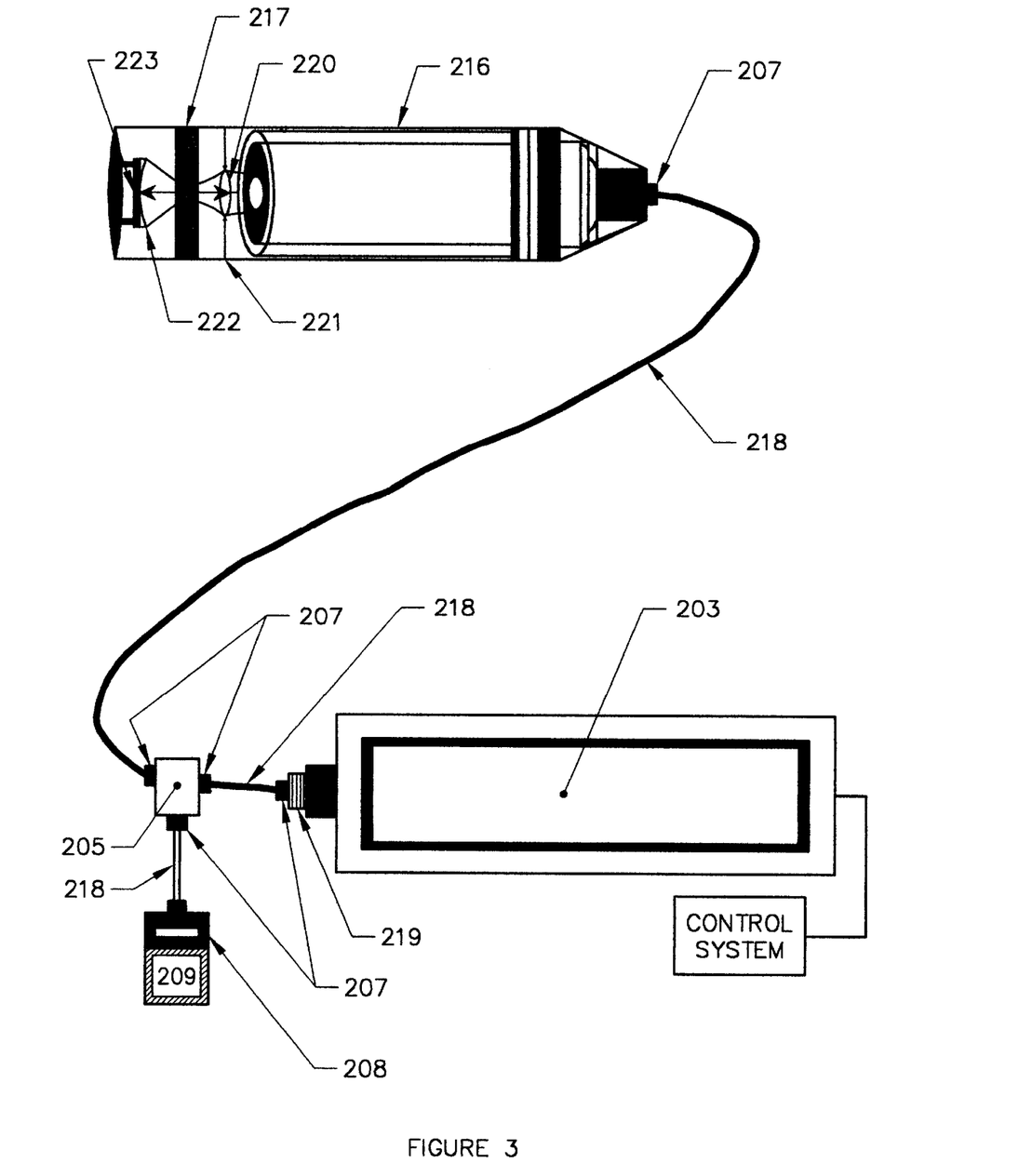
FIG. 3 is a block diagram illustrating the point-sensing, pen-sized analyzer embodiment of present invention.

FIG. 3 illustrates an exemplary schematic diagram of a pen-size probe and laser for point detection. The pen-size sensor 216 is swept through the air so that the sample to be analyzed passes through the ventilation port screen 217. Pulsed laser radiation emitted from the laser 203 is introduced into the fiber optic cable 218 by means of the laser position adapter, collimator, and proximal focusing lens 219. The laser beam transmitted through the fiber optic 218 is then focussed with lens 220 on mount 221. Each fiber optic cable has coupling ends 207 for connection.

If the analyte or target molecule is present in an air sample, then photofragmentation with subsequent excitation resulting in amplified stimulated emission occurs, as described above, and collected. As the emission is coaxial and bidirectional, a mirror 222 on positioner 223 is used to reflect the emission propagated in the forward direction. The forward and reverse emissions are then transmitted via fiber optic cable 218 back to the detector 209.

The return emissions through the fiber optic path 218 are first propagated to the substrate with antireflecting laser coating 205, directed to an interference filter 208, and are detected by a photodetector 209. A voltage supply powering the photodetector 209 is not shown. System control, signal processing, as well as data acquisition and analysis, which are not shown, are accomplished as for the remote sensor embodiment.

VALIDATION OF THE PF/SE APPROACH

Presented in Table 1 are the two-photon allowed transitions of Br in the range 231.40–281.77 nm calculated using energies and term symbols reported by Moore, "Atomic Energy Levels," Vol. II, NBS, U.S. Government Printing Office, Washington, DC, 1952, included by reference. By investigating this spectral region, a strong Br atom signal was observed at 260.634 nm, which corresponds to the spin forbidden $4p^45p\ ^4D°_{3/2} \leftarrow 4p^5\ ^2P°_{3/2}$ transition. Although other Br excitation wavelengths were observed, the transition at 260.634 nm proved to be the best for analytical measurements, primarily because of the combined efficiencies of the dye and doubling crystal near 260 nm.

TABLE 1

A table of Br two-photon transitions in the 231.4–281.8 nm range.

| TRANSITION | | | λ (nm) | TRANSITION | | | λ (nm) |
|---|---|---|---|---|---|---|---|
| $^4P°_{5/2}$ | ← | $^2P°_{1/2}$ | 281.77 | $^4P°_{1/2}$ | ← | $^2P°_{1/2}$ | 243.58 |
| $^4P°_{3/2}$ | ← | $^2P°_{1/2}$ | 280.44 | $^4D°_{5/2}$ | ← | $^2P°_{1/2}$ | 243.52 |
| $^4D°_{5/2}$ | ← | $^2P°_{1/2}$ | 277.76 | $^4D°_{3/2}$ | ← | $^2P°_{1/2}$ | 243.15 |
| $^4P°_{1/2}$ | ← | $^2P°_{1/2}$ | 277.31 | $^4D°_{1/2}$ | ← | $^2P°_{1/2}$ | 241.71 |
| $^4D°_{3/2}$ | ← | $^2P°_{1/2}$ | 273.78 | $^2P°_{3/2}$ | ← | $^2P°_{1/2}$ | 239.33 |
| $^4D°_{1/2}$ | ← | $^2P°_{1/2}$ | 268.87 | $^2P°_{1/2}$ | ← | $^2P°_{1/2}$ | 238.64 |
| $^4P°_{5/2}$ | ← | $^2P°_{3/2}$ | 267.86 | $^4P°_{3/2}$ | ← | $^2P°_{1/2}$ | 235.87 |
| $^2D°_{5/2}$ | ← | $^2P°_{1/2}$ | 267.31 | $^2P°_{1/2}$ | ← | $^2P°_{1/2}$ | 235.66 |
| $^4S°_{3/2}$ | ← | $^2P°_{1/2}$ | 266.72 | $^2P°_{5/2}$ | ← | $^2P°_{1/2}$ | 235.32 |
| $^4P°_{3/2}$ | ← | $^2P°_{3/2}$ | 266.66 | $^2D°_{3/2}$ | ← | $^2P°_{1/2}$ | 234.86 |
| $^2P°_{1/2}$ | ← | $^2P°_{1/2}$ | 266.05 | $^4S°_{3/2}$ | ← | $^2P°_{1/2}$ | 234.57 |
| $^2P°_{3/2}$ | ← | $^2P°_{1/2}$ | 264.95 | $^2D°_{5/2}$ | ← | $^2P°_{1/2}$ | 234.36 |
| $^4D°_{7/2}$ | ← | $^2P°_{3/2}$ | 264.85 | $^4S°_{1/2}$ | ← | $^2P°_{1/2}$ | 234.04 |
| $^4D°_{5/2}$ | ← | $^2P°_{3/2}$ | 264.23 | $^4P°_{5/2}$ | ← | $^2P°_{3/2}$ | 233.86 |
| $^4P°_{1/2}$ | ← | $^2P°_{3/2}$ | 263.83 | $^4P°_{3/2}$ | ← | $^2P°_{3/2}$ | 233.70 |
| $^2D°_{3/2}$ | ← | $^2P°_{1/2}$ | 263.14 | $^4D°_{7/2}$ | ← | $^2P°_{3/2}$ | 233.22 |
| $^2S°_{1/2}$ | ← | $^2P°_{1/2}$ | 262.55 | $^4P°_{1/2}$ | ← | $^2P°_{3/2}$ | 233.12 |
| $^4D°_{3/2}$ | ← | $^2P°_{3/2}$ | 260.63 | $^4D°_{5/2}$ | ← | $^2P°_{3/2}$ | 233.06 |
| $^4D°_{1/2}$ | ← | $^2P°_{3/2}$ | 256.18 | $^4P°_{5/2}$ | ← | $^2P°_{3/2}$ | 232.95 |
| $^2D°_{5/2}$ | ← | $^2P°_{3/2}$ | 254.76 | $^4D°_{3/2}$ | ← | $^2P°_{3/2}$ | 232.73 |
| $^4S°_{3/2}$ | ← | $^2P°_{3/2}$ | 254.23 | $^2P°_{1/2}$ | ← | $^2P°_{1/2}$ | 232.36 |
| $^2P°_{1/2}$ | ← | $^2P°_{3/2}$ | 253.62 | $^4P°_{3/2}$ | ← | $^2P°_{3/2}$ | 232.30 |
| $^2P°_{3/2}$ | ← | $^2P°_{3/2}$ | 252.62 | $^2D°_{5/2}$ | ← | $^2P°_{1/2}$ | 232.28 |
| $^2D°_{3/2}$ | ← | $^2P°_{3/2}$ | 250.98 | $^2D°_{3/2}$ | ← | $^2P°_{1/2}$ | 232.10 |
| $^2S°_{1/2}$ | ← | $^2P°_{3/2}$ | 250.43 | $^2P°_{3/2}$ | ← | $^2P°_{3/2}$ | 231.98 |
| $^4P°_{5/2}$ | ← | $^2P°_{1/2}$ | 244.39 | $^4P°_{1/2}$ | ← | $^2P°_{1/2}$ | 231.87 |
| $^4P°_{3/2}$ | ← | $^2P°_{1/2}$ | 244.22 | $^4D°_{1/2}$ | ← | $^2P°_{3/2}$ | 231.40 |

An estimate of the magnitude of the two-photon absorption cross section for the Br $4p^45p\ ^4D°_{3/2} \leftarrow 4p^5\ ^2P°_{3/2}$ transition is obtained by the following expression given by McIlrath, Hudson, Aiken, and Wilkenson, Applied Optics, Vol. 18, p. 316, 1979, $$\sigma_o^{(2)}(\omega) = \frac{\pi e^4}{8\epsilon_o^2 m^2 c^2} \frac{\omega^2}{\omega_1 \omega_2} \frac{f_1 f_2}{(\omega - \omega_1)^2} \quad (2)$$

where e is the electronic charge (C), m is the mass of the electron (kg), $\epsilon_o$ is the permittivity of free space (C²/(N m²)), c is the speed of light (m/s), $\omega_i$(i=1,2,1) is the angular frequency of the radiation (s⁻¹), and $f_i$ (i=1,2) is the absorption oscillator strength of the strongest transitions between the appropriate states. Substitution of the appropriate energies and oscillator strengths ($f_1$=0.199, $f_2$=0.513) into equation (2) yields a value of $3.8\times10^{-43}$m⁴. For comparison, McIlrath et al. have estimated the two-photon cross section for O atoms at 226 nm as $7.0\times10^{-44}$m⁴. This value is in good agreement with those predicted by more rigorous quantum mechanical methods, which include contributions from multiple intermediate states. Thus, the above expression is an approximation that is effective when the two-photon cross section is dominated by a single intermediate state. Lesser contributions by additional intermediate states are best accounted for by explicit quantum mechanical approaches, although such calculations require extensive computational capabilities.

The unit of $\sigma_o^{(2)}(\omega)$ is in m⁴ and is related to the generalized cross section by a normalized line-shape function, δ. In the limit of a relatively broad laser profile, the line-shape function is dominated by the laser bandwidth and is simply $1/(\delta\omega_{laser})$. In the present invention, the frequency doubled bandwidth (FWHM) of the laser is approximately 0.11 cm⁻¹ (1cm⁻¹=2.998×10¹⁰ sec⁻¹) yielding a value of the generalized cross section, $\sigma^{(2)}(\omega)$, of $1.8\times10^{-45}$cm⁴s at 260.634 nm.

Figure 4:
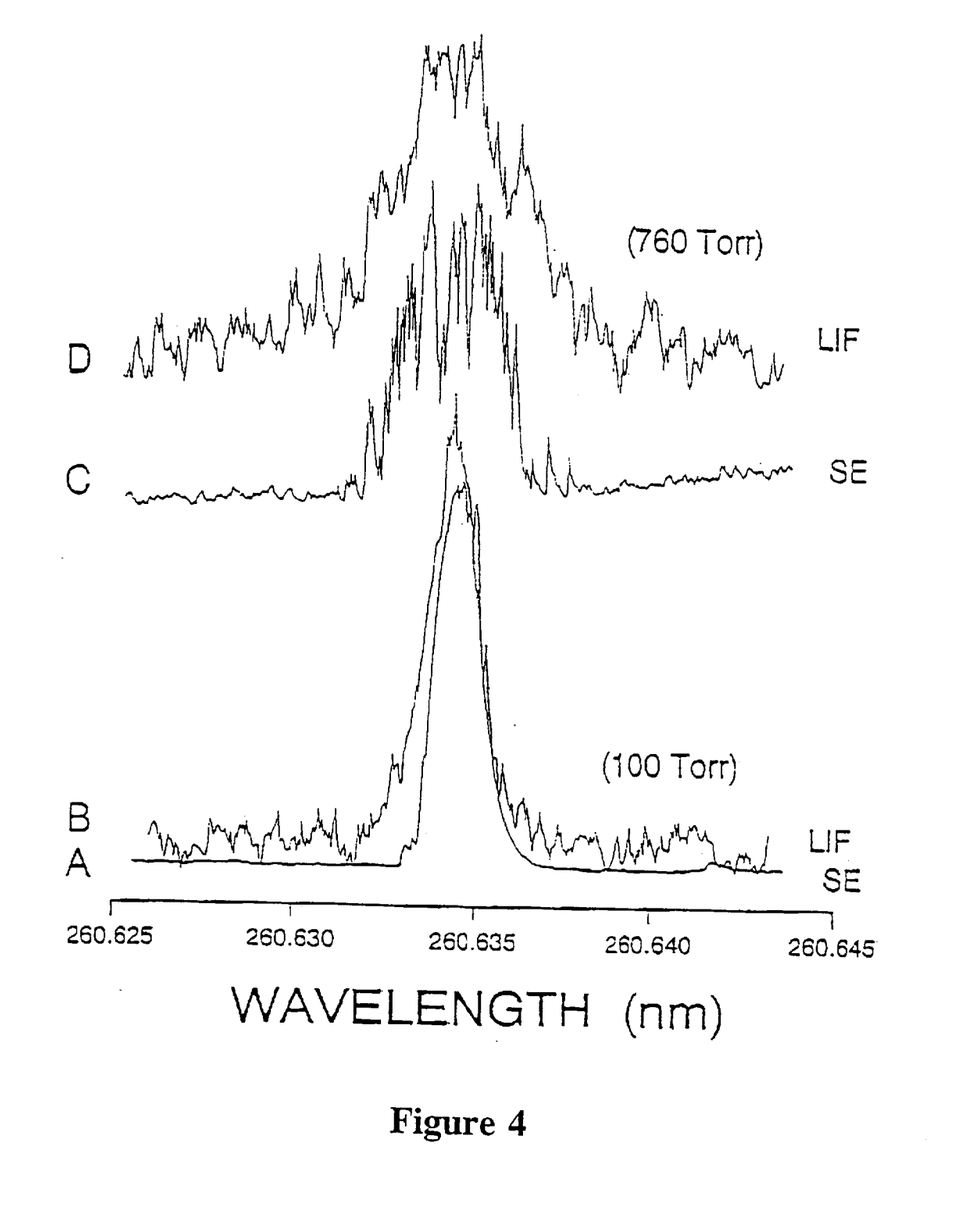
FIG. 4 illustrates normalized excitation profiles of Br atom (generated from $CHClBr_2$) at 100 Torr represented by lines A and B, and 760 Torr represented by lines C and D. Lines B and D correspond to PF/LIF, and lines A and C correspond to PF/SE.

Presented in FIG. 4 is the pressure dependence of the excitation profiles normalized for comparison as lines B and D for using LIF, and as lines A and C for using SE. Normalized excitation profile lines A and B were obtained at 100 Torr pressure. Normalized excitation profile lines C and D were obtained at 1 atmosphere (760 Torr) pressure. In the case of each technique, the profile is broadened at 1 atmosphere. The narrowness of the SE profile relative to the LIF is expected due to the exponential gain of the medium, which leads to a spectral narrowing of the profile. The spectra demonstrate the utility of the PF/SE approach, shown as lines A and C, for detecting halogenated compounds by monitoring the characteristic Br photofragment. The PF/SE approach is highly selective since it depends on the spectral selectivity of the laser as well as the characteristic atom. That is, in order to monitor the SE signal, both the laser and monochromator must be tuned to the proper atomic transitions. Thus, nonspecific interferences resulting from other atmospheric or tropospheric constituents are unlikely.

Figure 5:
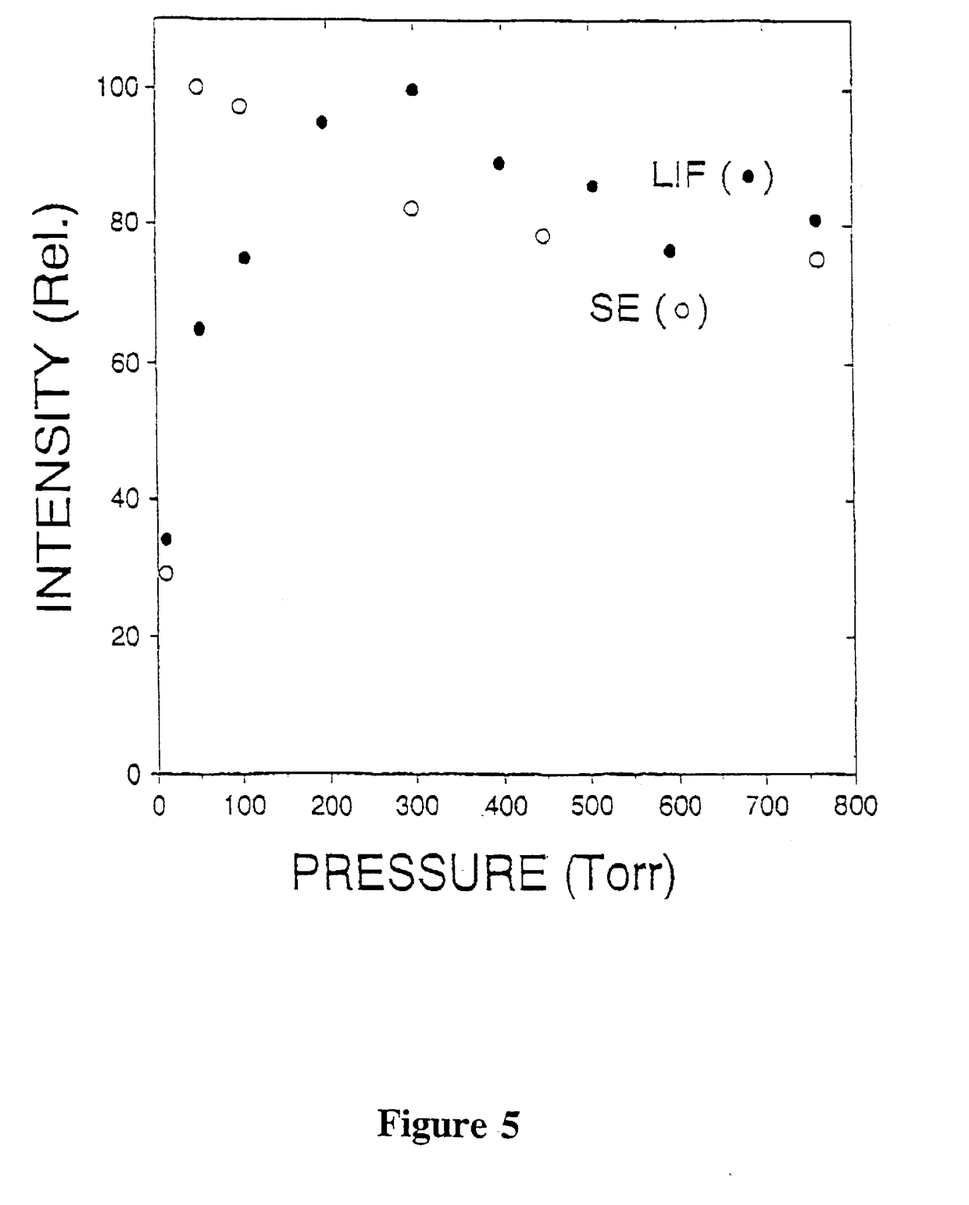
FIG. 5 is a graph illustrating pressure dependence of normalized signals for PF/LIF technique represented by filled circles and PF/SE technique represented by open circles.

Illustrated in FIG. 5 are open circles representing SE-detected signals as a function of the total cell pressure. For comparison, filled circles represent the LIF-detected signals as a function of the total cell pressure. It is important to note that for each pressure indicated in the FIG. 5, the mixing ratio of sample is constant, i.e., the analyte sample density changes with the pressure. It is observed that increased pressures reduce the sensitivities, although pressure influences the individual techniques differently. The pressure dependencies of these two techniques are similar, although the SE signal shows a steeper rise at lower pressures and faster decay at higher pressure than the LIF. The different pressure dependencies for LIF and SE are related to the effects of collisions on the SE line shape, where increased collisions broaden the line width and reduce the gain.

Presented in Table 2 are detection limits of $CHBr_3$ and $CHClBr_2$ obtained by LIF with the detector placed approximately 5 cm from the sample and SE with detector placed 2 m from the sample. For this study, the detection limits were defined as the signal equal to three times the noise of the background, determined as the standard deviation of 16 independent measurements of the background signal in $N_2$ measured off resonance at 260.64 nm. Measurement conditions were 100 Torr total pressure and laser energies ranging from 75–200 microJoules at 260 nm. The reported detection limits have been inferred from sensitivities determined for mixtures containing approximately 10 ppm of the specified compound in $N_2$, except for the SE where approximately 500 ppm mixtures were used. As shown in Table 2, detection limits in the ppm range can be obtained with SE with a relatively small amount of laser energy. An increase in sensitivity is projected with higher laser energy or using two, time-resolved lasers. For the latter case, one laser is used for photolysis while the other is used for atomic fragment excitation.

TABLE 2

The detection limits of $CHBr_3$ and $CHClBr_2$.

| | Detection Limits (ppm) | |
|---|---|---|
| Compound | Stimulated Emission (2 meters from sample) | LIF (5 cm. from sample) |
| $CHBr_3$ | 20 | 0.35 |
| $CHClBr_2$ | 10 | 0.25 |

The background noise of the SE approach, unlike that of LIF, is low and can be made even lower with appropriate shielding of the detector. In addition, since the signal is coherent and the background emission is incoherent, increasing the laser intensity to saturation conditions will greatly enhance the sensitivity without compromising the signal-to-noise ratio. The SE signal has other attributes that are unique due to its coherent nature. While the SE signal is coaxial with the laser, it can easily be separated with filters or prisms and, as it is bidirectional, it only requires "one window access" to the sample environment. This has important implications for accessing remote or hostile environments and also for coupling to fiber optic probes.

The present invention is a device for detecting and monitoring halogen containing compounds in the atmosphere or troposphere in real-time and in situ or remote. While particular embodiments of the present invention have been shown and described, it will be obvious to those skilled in the art that changes and modifications may be made without departing from the spirit and scope thereof. Therefore, it is intended that the claims herein are to include all such obvious changes and modifications as fall within the true spirit and scope of this invention.

What is claimed is:

1. An apparatus for real-time point detection and monitoring of halogenated compound, said apparatus comprising:

a means to generate a pulsed laser beam having a laser coupling end and a control interface, said laser beam having a wavelength capable of causing photofragmentation of halogenated compounds in an air sample and inducing stimulated emission of characteristic fragments, said stimulated emission being coaxial with said laser beam;

a first fiber optic cable having a first coupling end and a second coupling end for guiding said laser beam;

a collimator with one end coupled to the laser coupling end of the means to generate a laser beam and a second end coupled to the first coupling end of said first fiber optic cable, further comprising a lens assembly for focusing said laser beam to the first end of said first fiber optic cable;

a second fiber optic cable having a first coupling end and a second coupling end;

a third fiber optic cable having a first coupling end and a second coupling end;

a means to separate said coaxial stimulated emission from said laser beam, said means having first, second, and third coupling ends, which first coupling end is coupled to the second coupling end of said first fiber optic cable, which second coupling end is coupled to the first coupling end of said second fiber optic cable, and which third coupling end is coupled to the first coupling end of said third fiber optic cable, for directing laser beams and separating stimulated emissions onto the first coupling end of said third fiber optic cable;

an interference filter coupled to the second coupling end of said third fiber optic at one filter end and having a second filter end;

a photodetector coupled to the second filter end of said interference filter and having a detection output for electrically detecting said separated stimulated emissions; and a sensor coupled to the second coupling end of said second fiber optic cable, wherein said laser beam causes laser photofragmentation of said halogenated compounds in an air sample within said sensor and induces stimulated emission of characteristic fragment; and a control system coupled to said detection output of said photodetector and said control interface of said means to generate a laser beam, for control, signal processing, and data acquisition and analysis.

2. The apparatus of claim 1, wherein said sensor further comprises:
   a mounted focusing lens having a directed focal length along an optical path;
   a recess approximately coincident with and optically open to a portion of the optical path of the directed focal length of the mounted focusing lens, having a screened opening for intake of air samples having trace amounts of halogenated molecules; and
   a mirror on a mount optically facing said recess and said mounted focusing lens for reflecting a forward propagation of stimulated emission from characteristic fragment resulting from laser photofragmentation of halogenated molecules towards said second coupling end of said second fiber optic cable.

3. The apparatus of claim 1, wherein said control system is further comprised of a means for comparing spectral characteristics derived from the detection output with predetermined spectral characteristics of a known sample having a known concentration of contaminant admixed therewith.

4. The apparatus of claim 1, wherein said control system is further comprised of:
   a gated integrator receiving said detection output;
   an oscilloscope receiving said detection output;
   a laptop computer coupled to said gated integrator and said oscilloscope; and
   a printer connected to said laptop computer.

5. The apparatus of claim 1, wherein said means to separate stimulated emission from said laser beam comprises an electro-optic surface-coated substrate.

6. The apparatus of claim 1, wherein said means to separate stimulated emission from said laser beam comprises a prism arrangement.

7. A transportable apparatus for real-time remote detection and monitoring of halogenated compounds, said apparatus comprising:
   a means to generate a laser beam and having a control interface, said laser beam having a wavelength capable of causing photofragmentation of halogenated compounds in an air sample and inducing stimulated emission of characteristic fragments, said stimulated emission being coaxial with said laser beam;
   a laser reflecting means positioned to receive said laser beam and reflect said laser beam, resulting in a first reflected laser beam;
   a means to separate said coaxial stimulated emission from said laser beam having a first side to receive said first reflected laser beam and reflect to generate a second reflected laser beam and a second side to further transmit said coaxial stimulated emission transmitted from the first side;
   a curved mirror with a mount positioned to reflect and focus said second reflected laser beam towards a given exterior location of ambient air space for effecting a laser photofragmentation of halogenated compounds and inducing stimulated emission of characteristic fragment;
   an adjustable micropositioner coupled to the mount of the curved mirror for positioning said reflected and focused laser beam to a sensing location;
   an interference filter having a first side optically aligned to receive said coaxial stimulated emission transmitted from the first side through the second side of said means to separate said coaxial stimulated emission from said laser beam, and a second side to transmit a filtered radiation of said stimulated emission;
   a photodetector coupled to the second side of said interference filter and having a detection output for electrically detecting said filtered stimulated emissions;
   a power supply powering said photodetector; and
   a control system coupled to the detection output of said photodetector and the control interface of said means to generate a laser beam, for control, signal processing, and data acquisition and analysis.

8. The transportable apparatus of claim 7, wherein said control system comprises of a means for comparing spectral characteristics derived from the detection output with predetermined spectral characteristics of a known sample having a known concentration of contaminant admixed therewith.

9. The transportable apparatus of claim 7, wherein said control system comprises:
   a gated integrator receiving said detection output;
   an oscilloscope receiving said detection output;
   a laptop computer coupled to said gated integrator and said oscilloscope; and
   a printer connected to said laptop computer.

10. The transportable apparatus of claim 7, wherein said means to separate a stimulated emission from a laser beam comprises of a surface-coated quartz substrate.

11. The transportable apparatus of claim 7, wherein said means to separate a stimulated emission from a laser beam comprises of a prism arrangement.

12. An apparatus for real-time point detection of halogenated compounds, said apparatus comprising:
   means for generating a pulsed laser beam, said laser beam having a wavelength capable of causing photofragmentation of halogenated compounds in an air sample and inducing stimulated emission of characteristic fragments, said stimulated emission being coaxial with said laser beam;
   means for focusing said laser beam into a fiber optic means, said fiber optic means directing said laser beam to a target air sample;
   means for separating said coaxial stimulated emission from said laser beam and for directing said stimulated emission to an interference filter;
   a photodetector coupled to said interference filter; and
   means for controlling and conducting data acquisition, analysis and signal processing for said apparatus.

13. An apparatus for real-time remote detection of halogenated compounds, said apparatus comprising:
   means for generating a pulsed laser beam, said laser beam having a wavelength capable of causing photofragmentation of halogenated compounds in ambient air and inducing stimulated emission of characteristic fragments, said stimulated emission being coaxial with said laser beam;
   means for directing said laser beam to a target area;
   means for separating said coaxial stimulated emission from said laser beam and for directing said stimulated emission to an interference filter;
   a photodetector coupled to said interference filter; and
   means for controlling and conducting data acquisition, analysis and signal processing for said apparatus.

* * * * *